US010088404B2

(12) United States Patent
Dietrich et al.

(10) Patent No.: US 10,088,404 B2
(45) Date of Patent: Oct. 2, 2018

(54) METHOD FOR DETERMINING A PARTICLE SHAPE

(71) Applicant: PARSUM GESELLSCHAFT FUER PARTIKEL-, STROEMUNGS- UND UMWELTMESSTECHNIK MBH, Chemnitz (DE)

(72) Inventors: Stefan Dietrich, Chemnitz (DE); Dieter Petrak, Weimar (DE); Michael Koehler, Oberlungwitz (DE); Guenter Eckardt, Chemnitz (DE)

(73) Assignee: Parsum Gesellschaft fuer Partikel-, Stroemungs- und Umweltmesstechnik mbH, Chemnitz (DE)

( * ) Notice: Subject to any disclaimer, the term of this patent is extended or adjusted under 35 U.S.C. 154(b) by 0 days.

(21) Appl. No.: 15/318,691

(22) PCT Filed: Jun. 29, 2015

(86) PCT No.: PCT/IB2015/054857
§ 371 (c)(1),
(2) Date: Dec. 14, 2016

(87) PCT Pub. No.: WO2016/001816
PCT Pub. Date: Jan. 7, 2016

(65) Prior Publication Data
US 2017/0131196 A1 May 11, 2017

(30) Foreign Application Priority Data

Jul. 1, 2014 (DE) .................. 10 2014 109 166

(51) Int. Cl.
*G01N 15/02* (2006.01)
(52) U.S. Cl.
CPC ..... *G01N 15/0211* (2013.01); *G01N 15/0227* (2013.01); *G01N 2015/0294* (2013.01)

(58) Field of Classification Search
CPC .......... G01N 15/0205; G01N 15/0211; G01N 15/1459; G01N 2021/4716; G01N 15/1434
(Continued)

(56) References Cited

U.S. PATENT DOCUMENTS

| 4,871,251 A | 10/1989 | Preikschat et al. |
| 5,309,215 A | 5/1994 | Schumann |

(Continued)

FOREIGN PATENT DOCUMENTS

| DE | 232760 A1 | 2/1986 |
| DE | 260764 A1 | 10/1988 |

(Continued)

OTHER PUBLICATIONS

Mingzhong Li et al., "Obtaining Particle Size Distribution from Chord Length Measurements", pp. 170-174, Aug. 1, 2016.
(Continued)

*Primary Examiner* — Md M Rahman
(74) *Attorney, Agent, or Firm* — Laurence A. Greenberg; Werner H. Stemer; Ralph E. Locher

(57) ABSTRACT

A method for determining a shape of particles in a distribution with reduced measuring and analyzing complexity includes detecting the number of particles, measuring and storing a particle chord length for each particle as a measurement for particle size and measuring at least first and second distributions of the particle size from the particle chord length measured for each particle. The first distribution is based on a first quantity type, the second distribution is based on a second quantity type and the quantity types correspond to different powers of the particle size. A first distribution parameter, corresponding to a cumulative or density distribution, of the first distribution is set into a distribution parameter ratio with a second distribution
(Continued)

parameter, corresponding to a cumulative or density distribution, of the second distribution. An aspect ratio is determined from the distribution parameter ratio as a value characterizing the shape of the particles.

7 Claims, 2 Drawing Sheets

(58) Field of Classification Search
USPC .......................................................... 356/336
See application file for complete search history.

(56) References Cited

U.S. PATENT DOCUMENTS

| | | | |
|---|---|---|---|
| 5,764,358 A | 6/1998 | Heffels | |
| 6,061,130 A | 5/2000 | Plate et al. | |
| 6,449,042 B1 | 9/2002 | Hamann | |
| 7,907,279 B2 | 3/2011 | Seifert et al. | |
| 8,780,196 B2 | 7/2014 | Vennewald | |
| 2010/0179770 A1* | 7/2010 | Fuhrman | G01J 3/02 702/28 |
| 2011/0209392 A1* | 9/2011 | Kunik | C04B 7/4407 44/500 |
| 2012/0111117 A1* | 5/2012 | Prakash | G01N 29/032 73/599 |
| 2015/0186466 A1* | 7/2015 | Gaza | G06F 17/30466 707/714 |
| 2016/0299047 A1* | 10/2016 | Molla | B01L 3/502784 |

FOREIGN PATENT DOCUMENTS

| | | |
|---|---|---|
| DE | 278859 A1 | 5/1990 |
| DE | 4119240 C2 | 3/1993 |
| DE | 4129105 A1 | 3/1993 |
| DE | 4313688 A1 | 11/1994 |
| DE | 19628348 C1 | 9/1997 |
| DE | 69406683 T2 | 6/1998 |
| DE | 19802141 C1 | 4/1999 |
| DE | 102004056520 A1 | 6/2006 |
| DE | 60029878 T2 | 3/2007 |
| DE | 10218413 B4 | 9/2008 |
| DE | 102009056503 A1 | 6/2011 |
| EP | 1972921 A1 | 9/2008 |

OTHER PUBLICATIONS

Li M et al., "Determination of non-spherical particle size distribution from chord length measurements. Part 1: Theoretical analysis", pp. 3251-3265, Jun. 1, 2005.

Silva Ana F T et al., "Particle sizing measurements in pharmaceutical applications: Comparison of in-process methods versus off-line methods", pp. 1006-1018, Nov. 1, 2013.

* cited by examiner

METHOD FOR DETERMINING A PARTICLE SHAPE

BACKGROUND OF THE INVENTION

Field of the Invention

The invention relates to a method for determining a particle shape of particles provided in a distribution.

Besides the particle size, the particle shape is an important parameter in the particle technology being used for characterizing the particles utilized in the procedural methods. The particle shape influences the bulk density, the porosity, the flowability, the interaction with streams and other powder properties. For determining the particle shape, camera-based, diffractive or light-scattering-based methods are used. Form factors such as the circularity serve for describing the particle shape.

In camera-based methods, the particles are depicted as two-dimensional images onto the sensor of the camera. If the sensor is a CCD matrix or a CMOS image sensor, a corresponding image evaluation software for determining the particle shape is used. The document DE 198 02 141 C1 describes a solution with a matrix camera and in the document EP 1 972 921 A1, a solution with two cameras is described. If the sensor is a CCD cell, the depicted particle area is composed of the measured chord lengths at a known particle speed. Corresponding devices and methods are mentioned in the documents DE 10 2009 056 503 A1 (with sensor line), DE 10 2004 056 520 A1 (with CCD cell), DE 43 13 688 A1 (with CCD line), DE 41 19 240 C2 (with CCD line), DD 278 859 A1 (with CCD line sensor), DD 260 764 A1 (with CCD row sensor) and DD 232760 A1 (with single-spaced television camera). The document DE 196 28 348 C1 suggests determining the particle shape with a line of individual optical fibers, wherein a second optical fiber line is used for determining the speed.

Diffractive methods use the dependency of the particle diffraction picture of the particle shape. Thereby, the particles are irradiated with coherent light and the light intensity distribution of the diffraction picture is measured with a suitable receiver. The distribution of the light intensity in the diffraction picture depends on the shape of the particles. Solutions for this are disclosed in the documents DE 694 06 683 T2 (with ring sensor) and DE 102 18 413 B4.

The document DE 41 29 105 A1 discloses a determination of the particle shape by means of a light scattering measurement.

Thus, when using methods known from the prior art for determining the particle shape, either the entire particle image or at least several chords per particle are optically to be determined and evaluated. The measuring and analyzing complexity connected thereto is relatively high.

BRIEF SUMMARY OF THE INVENTION

Therefore, the object of the present invention is to provide a method for determining a particle shape of particles provided in a distribution with reduced measuring and analyzing complexity.

This object is solved by a method of the above-mentioned type in which the number of particles is detected; a particle chord length (x) is measured and recorded for each particle as a measurement for a particle size; at least one first and second distribution of the particle size is generated from the particle chord length measured for each particle, wherein the first distribution is based on a first quantity type and the second distribution is based on a second quantity type, and wherein the first and the second quantity type are quantity types corresponding to different powers of the particle size; a first distribution parameter, corresponding to a cumulative or density distribution of the first distribution is set into a distribution parameter ratio with a second distribution parameter, corresponding to a cumulative or density distribution of the second distribution; and an aspect ratio is determined from the distribution parameter ratio as a value characterizing the particle shape of the particles.

The method according to the invention thus assumes the measurement of chord lengths of the particles to be characterized as measurement for their particle size. Only one single chord length has to be detected and subsequently analyzed for each particle in the present invention. The chord length of moving particles can be determined with a single-point scanning, for instance.

In the method according to the invention, the single-point scanning can be done for example by means of a focused beam as is explained in the documents DE 600 29 878 T2 or U.S. Pat. No. 4,871,251. In another variant of the single-point scanning, which is mentioned for instance in the document DE 196 28 348 C1, the two-dimensional shadow image of a moving particle is scanned by means of an optical fiber.

In the method according to the invention, the single-point scanning can be done in a probe for the in-line determination of the size of moved particles in transparent media.

Due to the varying spatial position of the respective particle concerning its shape to be characterized in the method according to the invention with regard to the solid position of a scanning optical device, such as a scanning optical fiber, the measured chord length is related to a differing chord length of the particle. For a particle collective of several particles with regard to the particle shape to be characterized using the method according to the invention, thus one initially gets a chord length-frequency distribution as interim measuring result in the method according to the invention.

In the present invention, a first distribution based on a first quantity type is initially generated by the measured particle chord lengths. This first distribution can be for example, but not limited to, a so-called $q_0(x)$ density distribution respectively $q_0(x)$ number distribution density or a $Q_0(x)$ cumulative distribution respectively $Q_0(x)$ cumulative number distribution, in which the frequency of the measured chord lengths is stated and/or represented according to their number. Furthermore, a second distribution based on a second distribution type is generated from the measured chord lengths in the method according to the invention. This second distribution can be for example, but not limited to, a so-called $q_3(x)$ density distribution respectively $q_3(x)$ volume distribution density or a $Q_3(x)$ cumulative distribution respectively $Q_3(x)$ cumulative volume distribution, in which the frequency of the measured chord lengths is stated and/or represented according to the determined volumes.

Thereupon, characteristic distribution parameters corresponding to a certain cumulative or density distribution are determined from both distributions and set in proportion to each other in the method according to the invention. Absolute values extractable from the distribution such as maximum values are also among the distribution parameters in the method according to the invention. Thus, the median value $x_{50,3}$ of the $Q_3(x)$ cumulative distribution and the median value $x_{50,0}$ of the $Q_0(x)$ cumulative distribution can be, for example, but not limited to, determined and these median values can be set in proportion to each other, which is generally called, that is independent from the distribution parameters set in proportion to each other, as distribution parameter ratio.

In the present invention, the power of the quantity types used to determine the first and the second distribution is different. The respective powers of the quantity types used can be for example the known natural powers such as 0, 1, 2, or 3, wherein the power 0 reflects a frequency or number distribution, the power 1 reflects a length distribution, the power 2 a distribution of space or surface distribution and the power 3 reflects a mass or volume distribution. In the method according to the invention, however, fractional powers of the quantity types and/or powers of the quantity types, being higher than the power 3, can also be used for determining the first and the second distribution.

In the present invention it has been found that there is a correlation between the chord length frequency distribution and the particle shape. In the present invention it has been particularly surprising, however, that the particle shape can be deduced from the distribution parameter ratio which is used in the method according to the invention for determining the particle shape. Hereby, the method according to the invention is used for determining the particle shape for the entire particle collective and not for every individual particle of the particle collective. Thus, the particle shape for the particle collective is the predominant particle shape in the particle collective.

In the method according to the invention it does not matter whether the distribution parameters, which are based on the quantity type with the higher power, are set in proportion to the distribution parameters, which are based on the quantity type with the lower power, for determining the distribution parameter ratio or vice versa, the distribution parameter, which are based on the quantity type with the lower power, are set in proportion to the distribution parameter, which are based on the quantity type with the higher power, for determining the distribution parameter ratio.

Regarding the particle shape to be determined, it is differentiated between a spherical shape and an ellipsoid particle shape in the present invention. The ellipsoid particle shape is thereby reviewed as proxy for an elongated particle shape. The ellipsoid particle shape, which is depictable by the shape of an ellipsoid shadow image, is characterized by the ratio of major axis and minor axis of the ellipsis. In the method according to the invention, not only particle shapes with a pure elliptical-shaped shadow image, but also rod-shaped or other essentially cylinder-shaped or basically in their shadow image elliptical-shaped particle shapes are subsumed by the ellipsoid particle shape. For an globular particle with an annular shadow image, there is an analytical solution for the chord frequency distribution, while there is a numeric solution for an ellipsoid particle with an elliptical-shaped shadow image for the chord frequency distribution (Paul A. Langston, Trevor F. Jones "Non-Spherical 2-Dimensional Particle Size Analysis from Chord Measurements using Bayes' Theorem", Particle & Particle Systems Characterization, Volume 18, Issue 1, Pages 12-21, February 2001).

The distribution parameter ration determined in the method according to the invention is preferably a nondimensional parameter by means of which an aspect ratio predominating the particle distribution and thus the predominating particle shape can be determined particularly easily. The aspect ratio represents a ratio of chord lengths, preferably particles axes, determined in different alignments of the measured particle respectively the measured particles. The aspect ratio is for example, but not limited to, the ratio between the long major axis of an elliptical-shaped shadow image of a particle and the short minor axis of the elliptical-shaped shadow image of the particle. When having predominantly spherical particles, the aspect ratio aims at the value 1.

In the present invention, however, a ratio of short to long axes of the particles can be used as aspect ratio. It is only necessary that a constant procedure, that is long to short or short to long, is used for the respective calculation for determining the aspect ratio. In the present invention, the term aspect ratio also comprises the size ratio otherwise referred to as elongation.

The method according to the invention shows a particularly high accuracy especially in such applications, in which the particles provided in the distribution are almost equal, thus in which the particles to be characterized are provided in a monodisperse distribution, for example. The method according to the invention, however, is also applicable, if differently sized particles are provided in the distribution. Hereby, it only has to be considered that the uncertainty of the aspect ratio measured according to the invention increases with greater particle size differences of the particles.

According to a preferred embodiment of the method according to the invention, the first quantity type, as mentioned above, indicates a cumulative number distribution or density number distribution, that is a $Q_0(x)$ distribution or a $q_0(x)$ distribution, and the second quantity type indicates a cumulative volume distribution $Q_3(x)$ or volume density distribution $q_3(x)$. It also possible, however, that vice versa the first quantity type indicates a cumulative volume distribution $Q_3(x)$ or volume density distribution $q_3(x)$, while the second quantity type indicates a cumulative number distribution or number density distribution, that is a $Q_0(x)$ distribution or a $q_0(x)$ distribution. These quantity types are easily determinable and/or they are already available to the user of the method according to the invention due to the previous determination of the particle size and thus can be simply reused for determining the particle shape according to the present invention. As already mentioned above, the method according to the invention, however, is not limited to the use of these specific distributions.

In an advantageous variant of the method according to the invention, the first distribution is cumulative number distribution and the first distribution parameter is a fineness feature, in which the cumulative number distribution assumes a predetermined percentage value; and the second distribution is a cumulative volume distribution and the second distribution parameter a fineness feature, in which the cumulative volume distribution assumes the predetermined percentage value. Contrariwise, it is also possible in this embodiment of the invention that the first distribution is a cumulative volume distribution and the first distribution parameter is a fineness feature, in which the cumulative volume distribution assumes the predetermined percentage value; and that the second distribution is a cumulative number distribution and the second distribution parameter is a fineness feature, in which the cumulative number distribution assumes a predetermined percentage value. The percentage value predetermined for the fineness feature is hereby variable from 0 up to 100%.

In a specific embodiment of this variant of the method according to the invention, to the fineness feature is a median value, that is, an average value of the cumulative volume distribution or cumulative number distribution, in which 50% of the values of the respective distribution are smaller and 50% are larger than this average value. Here, for example, the median value $x_{50,0}$, at which the number distribution sum assumes the value 50%, can be used as first distribution parameter, and the median value $x_{50,3}$, at which the volume distribution sum assumes the value 50%, can be used as second distribution parameter.

In an alternative, equally advantageous embodiment of the method according to the invention, the first distribution is a number density distribution and the first distribution parameter is a modal value, at which the number density distribution assumes a maximum, and the second distribution is a volume density distribution and the second distribution parameter a modal value, at which the volume density distribution assumes a maximum. Contrariwise, it is also possible in this embodiment of the invention that the first distribution is a volume density distribution and the first distribution parameter is a modal value, at which the volume density distribution assumes a maximum, and the second distribution is a number density distribution and the second distribution parameter is a modal value, at which the number density distribution assumes a maximum. In this embodiment of the method according to the invention, for example, the first distribution parameter can be the modal value $x_{mod,(q0)}$, at which the number density distribution has a maximum, while the second distribution parameter can be the modal value $x_{mod,(q3)}$, at which the volume density distribution has a maximum or vice versa.

In another, equally advantageous embodiment of the method according to the invention it is provided that the first distribution is a number density distribution and the second distribution is also a number density distribution, and the first distribution parameter is a modal value, at which the number density distribution assumes a maximum, and the second distribution parameter is the largest measured chord length of the number density distribution. Contrariwise, it is also possible in this embodiment of the invention that the first distribution parameter is the largest measured chord length of the number density distribution, and the second distribution parameter is a modal value, at which the number density distribution assumes a maximum. In this embodiment of the invention, for example, the modal value $x_{mod,(q0)}$, at which the number density distribution has a maximum, can be used as first distribution parameter, and $x_{max}$, that is the largest chord length provided in the distribution, can be used as second distribution parameter, or vice versa.

The method according to the invention is suitable for example for determining a particle shape change during coating the particles.

BRIEF DESCRIPTION OF THE SEVERAL VIEWS OF THE DRAWING

Preferred embodiments of the present invention are explained in more detail in the following by means of figures, wherein.

DESCRIPTION OF THE INVENTION

Figure 1:
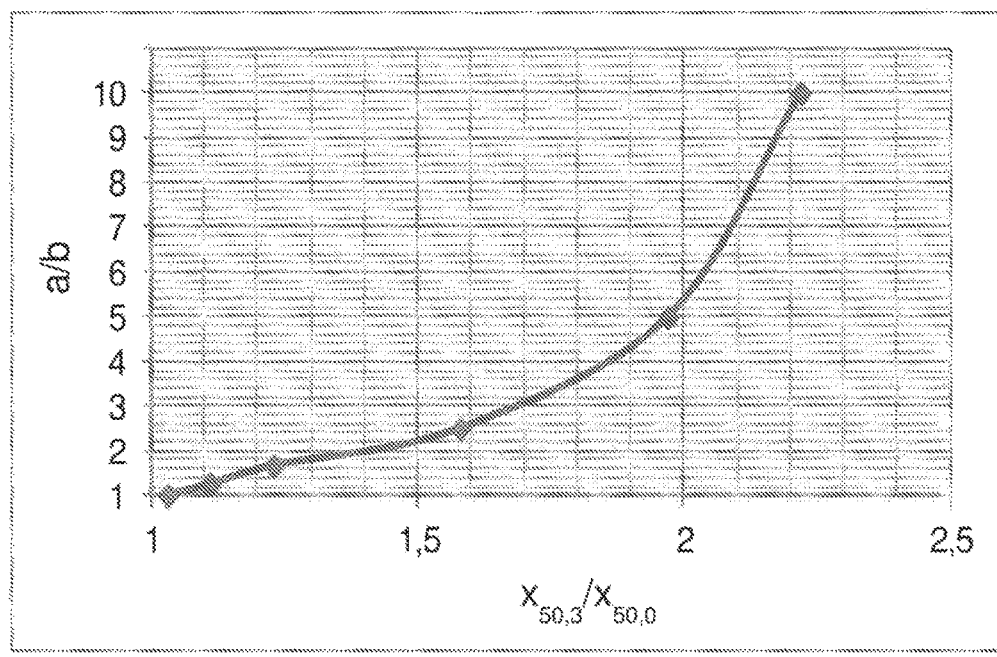
FIG. 1 shows a diagram, in which by means of an example the aspect ratio of particles is depicted by changing relatively to the ratio of the median values from cumulative volume distribution and cumulative number distribution.

FIG. 1 shows a diagram, in which by means of an example the ratio of the median value $x_{50,3}$ of the cumulative volume distribution to the median value $x_{50,0}$ of the cumulative number distribution is plotted on the x-axis, while on the y-axis, the aspect ratio a/b, that is the size ratio between elongated particle axis a and short particle axis b, of a distribution of ellipsoid particles is plotted. It is recognizable from this depiction that when the ratio $x_{50,3}/x_{50,0}$ is approaching the value 1, the ratio a/b also tends to 1, that is the particle shape approximates the spherical shape. The larger the ratio $x_{50,3}/x_{50,0}$, the more elongated is the particle shape.

Figure 2:
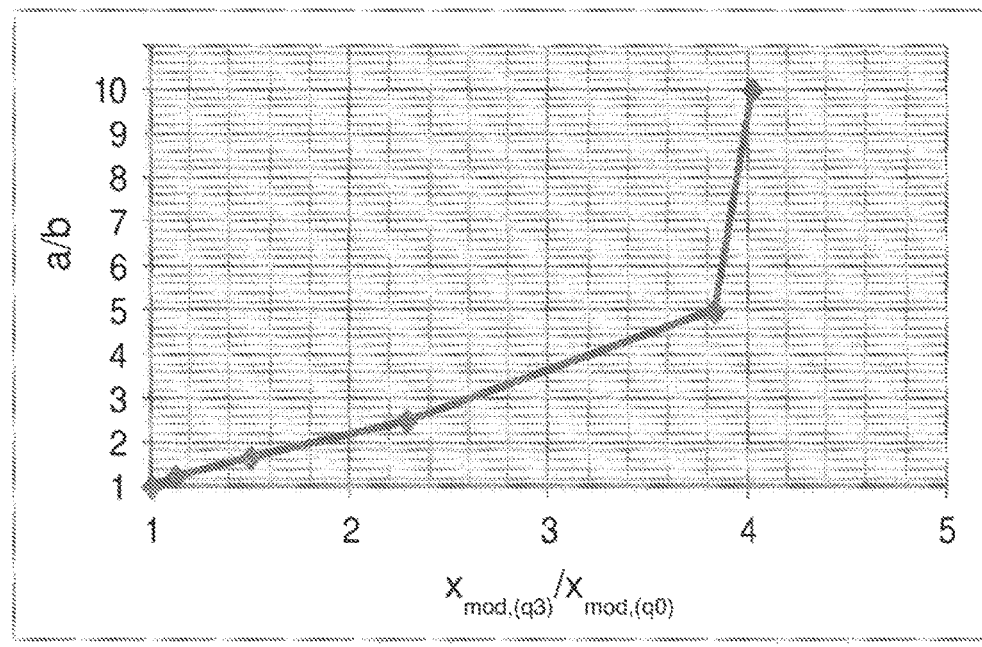
FIG. 2 shows a diagram, in which by means of an example the aspect ratio of particles is depicted by changing relatively to the ratio of the modal values from volume density distribution and number density distribution.

FIG. 2 shows a diagram, in which by means of an example the ratio of the modal value $x_{mod,(q3)}$ of the volume density distribution to the modal value $x_{mod,(q0)}$ of the number density distribution is plotted on the x-axis, while on the y-axis, the aspect ratio a/b, that is the size ratio between elongated particle axis a to short particle axis b, of a distribution of ellipsoid particles is plotted. It is recognizable from this depiction that when the ratio $x_{mod,(q3)}/x_{mod,(q0)}$ tends to the value 1, the ratio a/b also tends to 1, that is the particle shape approximates the spherical shape. The larger the ratio $x_{mod,(q3)}/x_{mod,(q0)}$, the more elongated is the particle shape.

Figure 3:
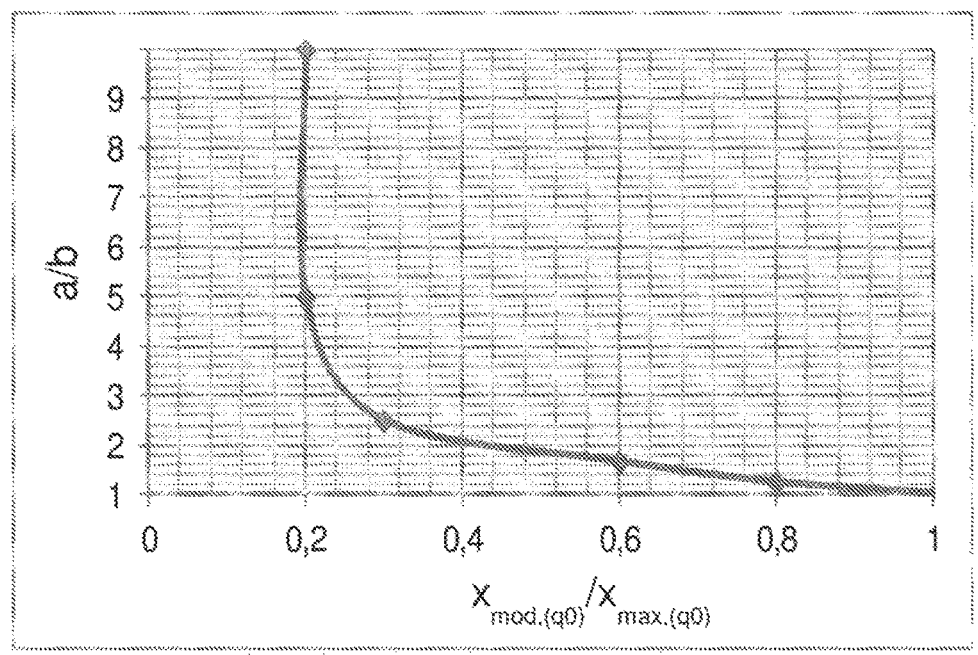
FIG. 3 shows a diagram, in which by means of an example the aspect ratio of particles is depicted by changing relatively to the ratio of the modal value of number density distribution and largest occurring chord length.

FIG. 3 shows a diagram, in which by means of an example the ratio of the modal value $x_{mod,(q0)}$ of the number density distribution to the largest occurring chord length $x_{max}$ is plotted on the x-axis, while on the y-axis, the aspect ratio a/b, that is the size ratio between long particle axis a to short particle axis b, of a distribution of ellipsoid particles, is plotted. Here, it is also recognizable that when the ratio $x_{mod,(q0)}/x_{max}$ tends to the value 1, the ratio a/b also tends to 1, that is the particle shape approximates the spherical shape. The lower the ratio $x_{mod,(q0)}/x_{max}$, the more elongated the particle shape.

The distribution parameters $x_{50,3}$, $x_{50,0}$, $x_{mod,(q3)}$, $x_{mod,q0)}$ and $x_{max}$ stated in the FIGS. 1 to 3 are determined using measured particle chord lengths, which are measured by the single-point scanning. As explained by way of example further above, the particle shape of the particle collective can be characterized by means of the aspect ratio and from the measured chord length distribution using the calculated nondimensional parameter $x_{50,3}/x_{50,0}$, $x_{mod,(q3)}/x_{mod,(q0)}$ respectively $x_{mod,(q0)}/x_{max}$. Thereby, a change of the particle shape from an ellipsoid particle shape into a spherical shape or also vice versa can be detected during the measurement time. Accordingly, the method according to the invention can be used for example in methods, in which spherical shaped or ellipsoid particles are coated. Particularly reliable measurement results are thereby produced, when the particles are provided in a nearly respectively approximated monodisperse starting distribution.

As can be inferred from the explanations above, instead of the distribution parameters used in the figures, also other numerous distribution parameters characterizing the respective distribution in various embodiments of the method according to the invention can be applied.

Further attention must be paid to that the embodiments of the invention depicted in the figures are only of exemplary character. Thus, in further embodiments of the invention for example in addition to the ratios mentioned above, inverted ratios such as the ratio of the median value $x_{50,0}$ of the cumulative number distribution to the median value $x_{50,3}$ of the cumulative volume distribution and/or the ratio of the modal value $x_{mod,(q0)}$ of the number density distribution to the modal value $x_{mod,(q3)}$ of the volume density distribution can be calculated and evaluated and/or can be plotted in the respective graphic illustration on the x-axis or the y-axis.

The invention claimed is:

1. A method for determining a particle shape of particles provided in a distribution, the method comprising the following steps:
    detecting a number of the particles with a probe;
    measuring and storing a particle chord length for each particle with the probe;
    generating at least one first and one second distribution of a particle size from the measured particle chord length, basing the first distribution on a first quantity type, basing the second distribution on a second quantity type, and providing the quantity types used for determining the first distribution and the second distribution with different power;
    setting a first distribution parameter, corresponding to a cumulative or density distribution, of the first distribution into a distribution parameter ratio with a second distribution parameter, corresponding to a cumulative or density distribution, of the second distribution; and
    determining an aspect ratio from the distribution parameter ratio as a value characterizing the particle shape of the particles;
    wherein:
        the first distribution is a $Q_0(x)$ cumulative distribution and the first distribution parameter is a fineness feature, at which a cumulative number distribution assumes a predetermined percentage value, and the second distribution is a $Q_3(x)$ cumulative distribution and the second distribution parameter is a fineness feature, at which a $Q_3(x)$ cumulative distribution assumes the predetermined percentage value, or
        the second distribution is a $Q_0(x)$ cumulative distribution and the second distribution parameter is a fineness feature, at which a cumulative number distribution assumes a predetermined percentage value, and the first distribution is a $Q_3(x)$ cumulative distribution and the first distribution parameter is a fineness feature, at which a $Q_3(x)$ cumulative distribution assumes the predetermined percentage value;
        the generating, setting and determining steps being performed by a processor connected to the probe, the processor running evaluation software to perform the steps.

2. The method according to claim 1, wherein:
    the first distribution is a $q_0(x)$ density distribution and the second distribution is a $q_3(x)$ density distribution, or
    the second distribution is a $q_0(x)$ density distribution and the first distribution is a $q_3(x)$ density distribution.

3. The method according to claim 1, wherein the fineness feature is a median value.

4. The method according to claim 1, wherein:
    the first distribution is a $q_0(x)$ density distribution and the first distribution parameter is a modal value, at which the $q_0(x)$ density distribution assumes a maximum, and the second distribution is a $q_3(x)$ density distribution and the second distribution parameter is a modal value, at which the volume density distribution assumes a maximum, or
    the second distribution is a $q_0(x)$ density distribution and the second distribution parameter is a modal value, at which the $q_0(x)$ density distribution assumes a maximum, and the first distribution is a $q_3(x)$ density distribution and the first distribution parameter is a modal value, at which the volume density distribution assumes a maximum.

5. The method according to claim 1, which further comprises determining a change of the particle shape when coating particles by using the method.

6. A method for determining a particle shape of particles provided in a distribution, the method comprising the following steps:
    detecting a number of the particles with a probe;
    measuring and storing a particle chord length for each particle with the probe;
    generating at least one first and one second distribution of a particle size from the measured particle chord lengths, providing the first distribution as a $q_0(x)$ density distribution and providing the second distribution as a $q_0(x)$ density distribution;
    setting a first distribution parameter, corresponding to a cumulative or density distribution of the first distribution into a distribution parameter ratio with a second distribution parameter, corresponding to a cumulative or density distribution of the second distribution;
        providing the first distribution parameter as a modal value, at which the $q_0(x)$ density distribution assumes a maximum, and providing the second distribution parameter as a largest measured chord length of the a $q_0(x)$ density distribution, or
        providing the second distribution parameter as a modal value, at which the $q_0(x)$ density distribution assumes a maximum, and providing the first distribution parameter as a largest measured chord length of the a $q_0(x)$ density distribution; and
    determining an aspect ratio from the distribution parameter ratio as a value characterizing the particle shape of the particles;
    the generating, setting and determining steps being performed by a processor connected to the probe, the processor running evaluation software to perform the steps.

7. The method according to claim 6, which further comprises determining a change of the particle shape when coating particles by using the method.

* * * * *